US008546371B2

(12) United States Patent
Zhou et al.

(10) Patent No.: US 8,546,371 B2
(45) Date of Patent: Oct. 1, 2013

(54) NANOPARTICLE FORMULATED GLYCOLIPID ANTIGENS FOR IMMUNOTHERAPY

(75) Inventors: Dapeng Zhou, Houston, TX (US); Chun Li, Missouri City, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 13/188,642

(22) Filed: Jul. 22, 2011

(65) Prior Publication Data

US 2012/0021050 A1      Jan. 26, 2012

Related U.S. Application Data

(63) Continuation-in-part of application No. PCT/CN2010/000100, filed on Jan. 22, 2010.

(60) Provisional application No. 61/146,725, filed on Jan. 23, 2009.

(51) Int. Cl.
*A01N 43/00* (2006.01)
*A61K 31/33* (2006.01)

(52) U.S. Cl.
USPC .......................................................... 514/183

(58) Field of Classification Search
None
See application file for complete search history.

(56) References Cited

U.S. PATENT DOCUMENTS

| | | | |
|---|---|---|---|
| 5,780,441 A | 7/1998 | Higa et al. | |
| 7,695,738 B2 * | 4/2010 | Lin et al. ...................... | 424/489 |
| 2003/0157135 A1 | 8/2003 | Tsuji et al. | |
| 2007/0238673 A1 | 10/2007 | Porcelli | |
| 2008/0206319 A1 * | 8/2008 | Ebensen et al. ............... | 424/450 |
| 2008/0254045 A1 | 10/2008 | Donda et al. | |
| 2009/0285851 A1 | 11/2009 | Kang et al. | |
| 2009/0317335 A1 | 12/2009 | Lin et al. | |

FOREIGN PATENT DOCUMENTS

| | | | |
|---|---|---|---|
| WO | WO2007/045469 | * | 4/2007 |
| WO | 2008115641 A2 | | 9/2008 |
| WO | WO2008/115641 | * | 9/2008 |
| WO | 2009051837 | | 4/2009 |

OTHER PUBLICATIONS

Kobayashi, E. et al., A Novel Immunomodulator, and its Antitumor Activities, Oncol Res.;7(10-11):529-34 (1995).
Kawano, T., et al., CD1d-Restricted and TCR-Mediated Activation of valpha14 NKT Cells by Glycosylceramides, Science Nov. 28;278(5343):1626-9 (1997).
Fujii, S., et al., Activation of Natural Killer T Cells by Alpha-Galactosylceramide Rapidly Induces the Full Maturation of Dendritic Cells In Vivo and Thereby Acts as an Adjuvant for Combined CD4 and CD8 T Cell Immunity to a Coadministered Protein, J Exp Med. Jul. 21;198(2):267-79 (2003).
Zhou, D., OX40 Signaling Directly Triggers the Antitumor Effects of NKT Cells, J Clin Invest. Nov.;117(11):3169-72 (2007).
Choi,Y.S., et al., Alpha-Galactosylceramide Enhances the Protective and Therapeutic Effects of Tumor Cell Based Vaccines for Ovarian Tumors, Vaccine Oct. 30;26(46):5855-63, Epub 2008 Sep. 2, 2008.
Huang, Y., et al., et al., Enhancement of HIV DNA Vaccine Immunogenicity by the NKT Cell Ligand, Alpha-Galactosylceramide,Vaccine Mar. 28;26(15):1807-16. Epub Feb. 20, 2008.
Ko, S.Y., et al., Mediastinal Lymph Node CD8alpha-DC Initiate Antigen Presentation following Intranasal Coadministration of Alpha-GalCer, Eur J Immunol Aug.;37(8):2127-37 (2007).
Youn, H.J., et al., A Single Intranasal Immunization with Inactivated Influenza Virus and Alpha-Galactosylceramide Induces Long-Term Protective Immunity Without Redirecting Antigen to the Central Nervous System Vaccine Jul. 9;25 (28):5189-98. Epub May 21, 2007.
Galli, G., et al., Invariant NKT Cells Sustain Specific B Cell Responses and Memory, Proc Natl Acad Sci U S A. Mar. 6;104(10):3984-9. Epub Feb. 27, 2007.
Ko, S.Y., et al., Alpha-Galactosylceramide Can Act as a Nasal Vaccine Adjuvant Inducing Protective Immune Responses Against Viral Infection and Tumor, J Immunol. Sep. 1;175(5):3309-17 (2005).
Silk, J.D., et al., Utilizing the Adjuvant Properties of CD1d-Dependent NK T Cells in T Cell-Mediated Immunotherapy, J Clin Invest. Dec.; 114(12):1800-11(2004).
Gonzalez-Aseguinolaza, G., et al., Natural Killer T Cell Ligand Alpha-Galactosylceramide Enhances Protective Immunity Induced by Malaria Vaccines, J Exp Med. Mar. 4;195(5):617-24 (2002).
Fujii, S., et al., Prolonged IFN-Gamma-Producing NKT Response Induced with Alpha-Galactosylceramide-Loaded Dcs, Nat Immunol. Sep.; 3(9):867-74. Epub Aug. 5, 2002.
Uldrich, A.P., et al., NKT Cell Stimulation with Glycolipid Antigen In Vivo: Costimulation-Dependent Expansion, Bim-Dependent Contraction, and Hyporesponsiveness to Further Antigenic Challenge, J Immunol. Sep. 1;175(5):3092-101 (2005).
Parekh, V.V., et al., Glycolipid Antigen Induces Long-Term Natural Killer T Cell Anergy in Mice, J Clin Invest. Sep.; 115 (9):2572-83(2005).
Lee, P.T., et al., Testing the NKT Cell Hypothesis of Human IDDM Pathogenesis, J Clin Invest. Sep.;110(6):793-800 (2002).
Heissmeyer, V., et al., Calcineurin Imposes T Cell Unresponsiveness Through Targeted Proteolysis of Signaling Proteins, Nat Immunol. Mar.;5(3):255-65. Epub Feb. 15, 2004.

(Continued)

*Primary Examiner* — Craig Ricci
*Assistant Examiner* — Jared D Barsky
(74) *Attorney, Agent, or Firm* — Parker Highlander PLLC (57) ABSTRACT

A composition for stimulating NKT cells to produce anti-cancer and anti-viral cytokines without causing anergy of NKT cells includes a glycolipid antigen and a nanoparticle conjugated with the glycolipid antigen. The glycolipid antigen and the nanoparticle are not antigenic in mouse and human being. The composition can further include covalent or non-covalent connection between the glycolipid antigen and the nanoparticle. The glycolipid antigen is alpha-galactosylceramide or an analog of that. The nanoparticle can be a polymer. A production method of the composition includes preparing a nanoparticle and a glycolipid antigen and loading the glycolipid antigen to the nanoparticle. The glycolipid antigen can be coated onto the surface of the nanoparticle or encapsulated within the nanoparticle. A method of stimulating NKT cells to produce anti-cancer and anti-viral cytokines without causing anergy of NKT cells is also provided.

13 Claims, 9 Drawing Sheets

(56) References Cited

OTHER PUBLICATIONS

Chang, D.H., et al., Sustained Expansion of NKT Cells and Antigen-Specific T Cells After Injection of Alpha-GalactosylCeramide Loaded Mature Dendritic Cells in Cancer Patients, J Exp Med. May 2;201(9):1503-17. Erratum in: J Exp Med. Oct. 2007;204(10):2487 (2005).

Zwiorek, K., et al., Delivery by Cationic Gelatin Nanoparticles Strongly Increases the Immunostimulatory Effects of Cpg Oligonucleotides, Pharm Res. Mar.;25(3):551-62. Epub Oct. 3, 2007 (2008).

Reddy, S.T. et al., Exploiting Lymphatic Transport and Complement Activation in Nanoparticle Vaccines, Nat Biotechnol. Oct.; 25(10):1159-64. Epub Sep. 16, 2007.

Uto, T., et al., Targeting of Antigen to Dendritic Cells with Poly(Gamma-Glutamic Acid) Nanoparticles Induces Antigen-Specific Humoral and Cellular Immunity, J Immunol. Mar. 1;178(5):2979-86 (2007).

Zhou, D., et al., Lysosomal Glycosphingolipid Recognition by NKT Cells, Science Dec. 3;306(5702):1786-9. Epup Nov. 11, 2004.

Liu, Y., et al., A Modified Alpha-Galactosyl Ceramide for Staining and Stimulating Natural Killer T Cells, J Immunol Methods. May 30;312(1-2):34-9. Epub Mar. 6, 2006.

Overwijk, W.W., et al., Tumor Regression and Autoimmunity After Reversal of a Functionally Tolerant State of Self-Reactive CD8+ T Cells, J Exp Med. Aug. 18;198(4):569-80 (2003).

* cited by examiner

Step 1): SYNTHESIS OF COMPOUND A FROM PHYTOSPHINGOSINE.

FIG.5A

Step 3): SYNTHESIS OF 6-aminoethoxy-6-deoxy-alpha-galactosylceramide FROM COMPOUND A AND B.

NANOPARTICLE FORMULATED GLYCOLIPID ANTIGENS FOR IMMUNOTHERAPY

CROSS-REFERENCE TO RELATED APPLICATION(S)

This application is a continuation-in-part of International Patent Application PCT/CN2010/000100, now published in English as WO/2010/083728, filed Jan. 22, 2010, which claims the benefit of U.S. Provisional Application 61/146,725, filed Jan. 23, 2009. The aforementioned applications are hereby incorporated by reference

STATEMENT REGARDING FEDERALLY SPONSORED RESEARCH OR DEVELOPMENT

None.

THE NAMES OF THE PARTIES TO A JOINT RESEARCH AGREEMENT

None.

THE INCORPORATION-BY-REFERENCE OF MATERIAL SUBMITTED ON A COMPACT DISC

None.

FIELD OF THE INVENTION

The present invention relates to a novel nanoparticle formulated glycolipid antigen which has a strong activity to trigger the immune system to release anticancer and antiviral cytokines. In contrast to previously invented glycolipid antigens, said novel nanoparticle formulated glycolipid antigen does not cause the allergy (non-responsiveness after stimulation) of the immune system and can be used repeatedly to treat long term illness such as cancer and chronic viral diseases.

BACKGROUND OF THE INVENTION

This section provides background information related to the present disclosure which is not necessarily prior art.

Activation of innate immunity is critical for vaccine development and immunotherapy, through triggering antigen specific immune responses. Natural Killer T cells ("NKT cells") are a unique type of innate immune cells and a unique subset of lymphocytes that have markers and functions of T cells and NK cells. NKT cells can be activated within 2 hours of antigen (alpha-galactosylceramide) stimulation, and produce large amount of Th1 and Th2 cytokines. In addition to secreting cytokines, NKT cells play an extremely important role in initiating the cell-to-cell contact and crosstalk between several types of immune cells, including dendritic macrophages, CD4 T cells and CD8 T contrast to conventional T cells which recognize peptide antigens, invariant NKT cells recognize lipid antigens presented by the non-polymorphic MHC-like molecule CD1d.

Alpha-Galactosylceramide (KRN7000)

Alpha-galactosylceramide (αGalCer, also named as KRN7000), a potent immunotherapeutic, is a marine-sponge derived glycosphingolipid, such as the embodiment shown in U.S. Pat. No. 5,780,441. It is a super-agonist antigen for NKT cells and capable of limiting melanoma metastasis and inhibiting the replication of hepatitis B virus in mouse models through a Th1 cytokine (IFN-γ) mediated mechanism. In several clinical trials involving cancer patients and hepatitis C patients, alpha-galactosylceramide has been demonstrated to induce strong Th1 cytokine response.

Soluble Alpha-Galactosylceramide Induces Anergy NKT Cells

Figure 1A:
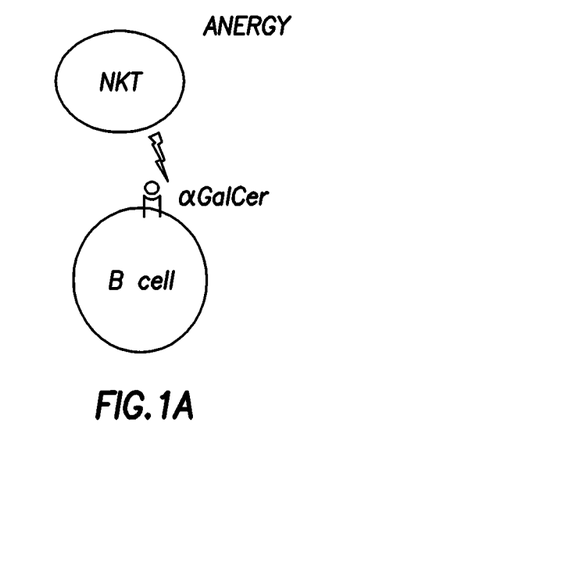
FIG. 1A, FIG. 1B, and FIG. 1C are perspective views of three forms of alpha-galactosylceramide.

A major problem for alpha-galactosylceramide is it causes NKT cells non-responsiveness (anergy) after one dose of treatment, because alpha-galactosylceramide can be presented by CD1d expressing B cells in the peripheral blood as shown in FIG. 1A, thus stimulates the NKT cells without proper co-stimulatory molecules.

Figure 1B:
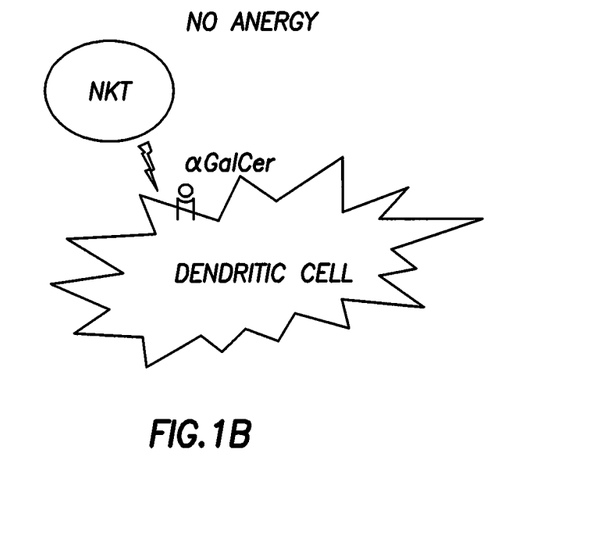

To overcome the anergy induced by soluble alpha-galactosylceramide, Dhodapkar and Steinmann have developed a cell therapy approach as shown in FIG. 1B, by intravenously injecting alpha-galactosylceramide pulsed, ex vivo generated dendritic cells from patients' peripheral blood mononuclear cells. The cell therapy method avoided the NKT anergy mechanism, and showed potent efficacy in cancer patients in eliciting tumor antigen-specific CD8 responses. However, cell therapy is expensive, and impracticable for virus infected patients since their tissues are excluded from GM' processing. Hence, new methods are needed to stimulate NKT cells in vivo repeatedly and effectively.

Expansion, Contraction, and Memory Phase of NKT Cells after Drug Stimulation

Figure 2:
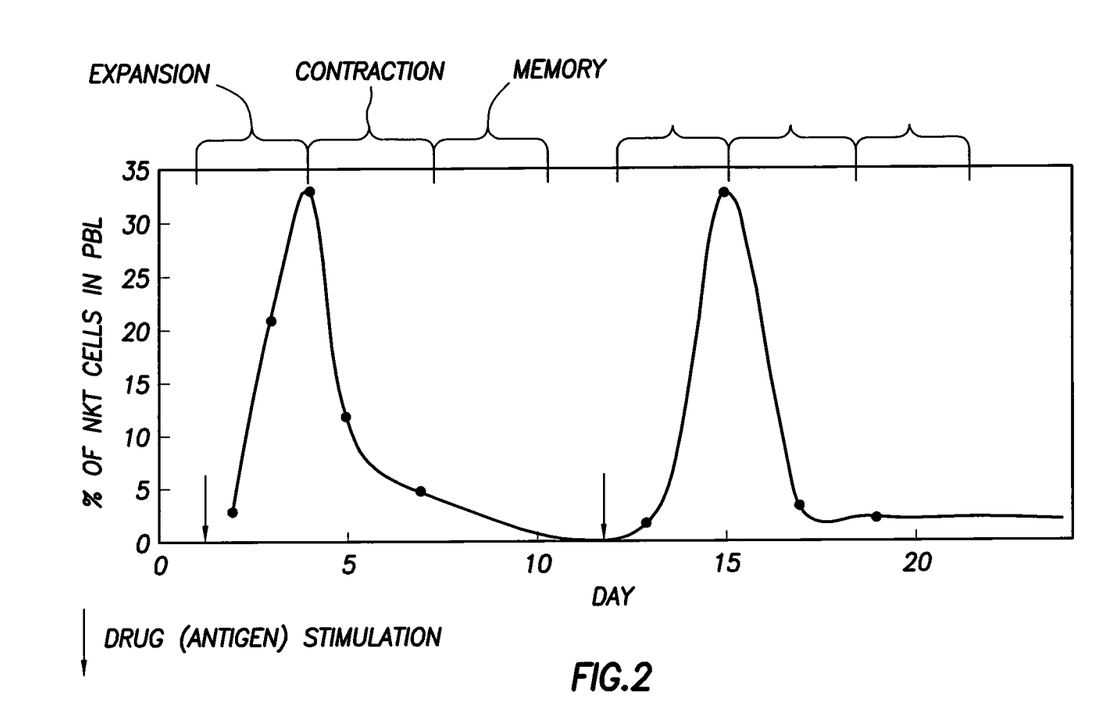
FIG. 2 is a perspective view of the expansion, contraction, and memory phases of NKT cells after being simulated by alpha-galactosylceramide.

As demonstrated in FIG. 2, the stimulation of NKT cells by a continuous release of alpha-galactosylceramide includes the expansion, contraction, and memory phases. In the expansion phase, the NKT cells produce anti-tumor and anti-viral cytokines. In contraction phase and memory phase, most NKT cells die, while 5 to 10% of "memory" NKT cells begin to "rest" and re-program themselves for the next stimulation. Thus a continuous release of alpha-galactosylceramide can not cause effective stimulation of NKT cells, instead, continuous release of alpha-galactosylceramide has been shown to cause the non-responsiveness (anergy) of NKT cells. Therefore, new methods are needed to cause rapid release of alpha-galactosylceramide upon being phagocytosed by dendritic cells and macrophages, but not consistent release of alpha-galactosylceramide to the serum.

SUMMARY OF THE INVENTION

This section provides a general summary of the disclosure, and is not a comprehensive disclosure of its full scope or its entire feature.

In one preferred embodiment, a composition for stimulating NKT cells to produce anti-cancer and anti-viral cytokines without causing anergy of NKT cells comprises a glycolipid antigen and a nanoparticle conjugated with the glycolipid antigen. The glycolipid antigen and the nanoparticle are not antigenic in mouse and human being.

In some embodiments, a composition for stimulating NKT cells to produce anti-cancer and anti-viral cytokines without causing anergy of NKT cells further comprises covalent or non-covalent connection between the glycolipid antigen and the nanoparticle.

In other embodiments, the glycolipid antigen is alpha-galactosylceramide.

In still other embodiments, the nanoparticle is polymer.

In another embodiment, the polymer is selected from the group consisting of PLGA, human albumin, polylactic acid, glycolic acid, polycaprolactone, polyester species, and any copolymers composed by 2 or more than 2 polymers mentioned above.

In still another embodiment, the nanoparticle comprising an acyl group exposed on the surface of the nanoparticle and capable of being utilized to conjugate with amine groups through an amide linkage.

In still another embodiment, the glycolipid antigen is a glycolipid analog of alpha-galactosylceramide with amine groups.

In still another embodiment, the glycolipid analog of alpha-galactosylceramide is selected from the group consisting of:
6-aminoethoxy-6-deoxy-alpha-galactosylceramide,
6-aminopropyl-6-deoxy-alpha-galactosylceramide,
6-aminobutyloxy-6-deoxy-alpha-galactosylceramide,
amino-acid-6-aminoethoxy-6-deoxy-alpha-galactosylceramide,
amino-acid-6-aminopropyl-6-deoxy-alpha-galactosylceramide,
amino-acid-6-aminobutyloxy-6-deoxy-alpha-galactosylceramide,
mini-PEG-6-aminoethoxy-6-deoxy-alpha-galactosylceramide,
mini-PEG-6-aminopropyl-6-deoxy-alpha-galactosylceramide, and
mini-PEG-6-aminobutyloxy-6-deoxy-alpha-galactosylceramide.

In one preferred embodiment, a method of stimulating NKT cells to produce anti-cancer and anti-viral cytokines without causing anergy of NKT cells comprises steps of providing a glycolipid antigen, providing a nanoparticle conjugated with the glycolipid antigen to form a nanoparticle formulated glycolipid antigen, loading the nanoparticle formulated glycolipid antigen into a phagocytic antigen presenting cell in a lysosome, recycling the nanoparticle formulated glycolipid antigen to the surface of the phagocytic antigen presenting cell, and utilizing the nanoparticle formulated glycolipid antigen to activate NKT cells repeatedly.

In some embodiments, the glycolipid antigen is alpha-galactosylceramide or analogs of alpha-galactosylceramide.

In still some embodiments, the phagocytic antigen presenting cell is a dendritic cell, or a macrophage.

In other embodiments, the nanoparticle is a polymer.

In still other embodiments, a method of stimulating NKT cells to produce anti-cancer and anti-viral cytokines without causing anergy of NKT cells further comprises the step of administering a therapeutically effective amount of the nanoparticle formulated glycolipid antigen to a patient in need thereof.

In one preferred embodiment, a production method of a nanoparticle formulated glycolipid antigen for stimulating NKT cells to produce anti-cancer and anti-viral cytokines without causing anergy of NKT cells comprises preparing a nanoparticle, preparing a glycolipid antigen, and loading the glycolipid antigen to the nanoparticle.

In some embodiments, the production method of a nanoparticle formulated glycolipid antigen for stimulating NKT cells to produce anti-cancer and anti-viral cytokines without causing anergy of NKT cells further comprises the step of coating the glycolipid antigen onto the surface of the nanoparticle.

In still some embodiments, the production method of a nanoparticle formulated glycolipid antigen for stimulating NKT cells to produce anti-cancer and anti-viral cytokines without causing anergy of NKT cells further comprises the step of directly encapsulating the nanoparticle and the glycolipid antigen together. The glycolipid antigen is substantially evenly distributed inside the nanoparticle.

In other embodiments, the glycolipid antigen is alpha-galactosylceramide or analogs of alpha-galactosylceramide.

In still other embodiments, the nanoparticle is polymer.

In another embodiment, the glycolipid antigen is a 6-aminoethoxy-6-deoxy-alpha-galactosylceramide.

In still another embodiment, the 6-aminoethoxy-6-deoxy-alpha-galactosylceramide is synthesized from compounds from a Phytosphingosine and a 1,2,3,4-DI-O-ISOPROPYLIDENE-α-D-GALACTOPYRANOSE.

BRIEF DESCRIPTION OF THE DRAWINGS

The drawings described herein are for illustrating purposes only of selected embodiments and not all possible implementation and are not intended to limit the scope of the present disclosure.

DETAILED DESCRIPTION OF THE PREFERRED EMBODIMENT

The following description of the preferred embodiment is merely exemplary in nature and is no way intended to limit the invention, its application, or uses. Example embodiments will now be described more fully with reference to the accompanying drawings.

The object of this invention is to provide a novel nanoparticle formulated glycolipid antigen, which can avoid being taken by B cells and stimulate immune system repeatedly in long term treatment of cancer and chronic viral infection status. The nanoparticle formulated glycolipid antigen can repeatedly stimulate NKT cells to produce IFN-γ, which is a cytokine with potent anticancer and antiviral activities. A novel drug with the present invention has been proved to have anticancer effects in a mouse model of tumor metastasis.

Figure 1C:
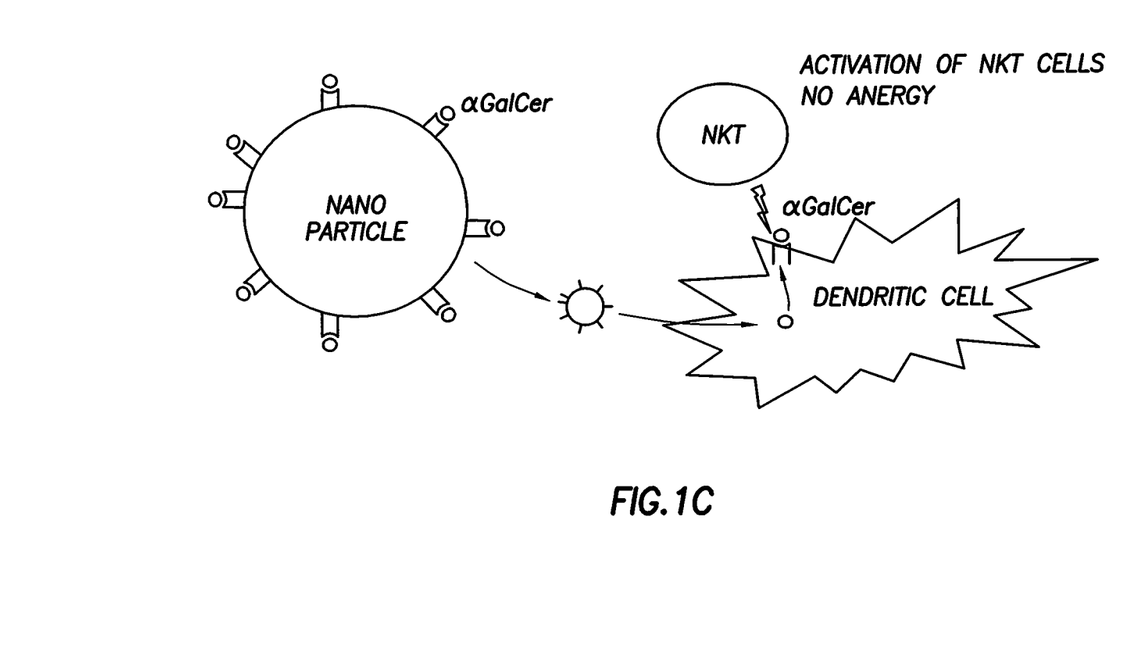

Characteristics and Structure of Nanoparticle Formulated Alpha-Galactosylceramide FIG. 1C illustrates a perspective view of a nanoparticle formulated alpha-galactosylceramide in accordance with an embodiment of the present invention. The nanoparticle formulated αGalCer is designed to be preferentially taken up by dendritic cells, released in the lysosome, and recycled to cell surface, which stimulate NKT cells without causing anergy. Specifically, alpha-galactosylceramide is loaded to the antigen presenting molecule, CD1d (a non-MHC antigen presenting molecule), in the lysosome; and recycled to cell surface, which activates NKT cells.

There are two approaches for our consideration to load alpha-galactosylceramide nanoparticles: 1) surface coating, which means we synthesize nanoparticles first, and conjugate alpha-galactosylceramide to the surface of nanoparticles; 2) direct encapsulating approach, which means to mix alpha-galactosylceramide and polymer together, and form the nanoparticles with alpha-galactosylceramide evenly distributed inside the nanoparticles. If encapsulation approach is used, the nanoparticle itself preferably have an in vivo half life shorter than 24 hours to allow release and clearance of alpha-galactosylceramide in the early expansion phase of NKT cells as shown in FIG. 2. Nanoparticles used to encapsulate alpha-galactosylceramide is preferably based on molecules degraded within 48 hours after intravenous injection.

In some embodiments, biodegradable polymer based nanoparticles can be chosen to be conjugated with alpha-galactosylceramide by either covalent or non-covalent interactions. Polymers, such as poly(lactic-co-glycolic acid) PLGA, human albumin, polylactic acid, glycolic acid, polycaprolactone, polyester species, as well as any copolymers composed by 2 or more than 2 polymers mentioned above, have excellent biocompatibility, biodegradability, commercial availability, and can be applied for delivering drugs such as proteins, peptide vaccines, and hydrophobic anticancer drugs.

Figure 3:
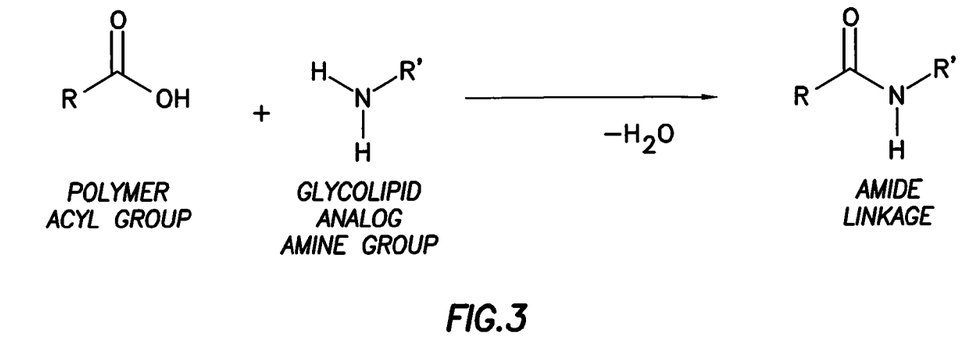
FIG. 3 is a perspective view of the structures of alpha-galactosylceramide analogs. Component 2 (containing amine group or free hydroxyl group) is conjugated to the surface of Component 1 (containing acyl group) through amide linkage.
Figure 4A:
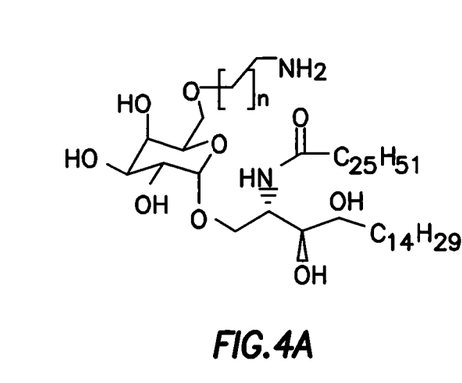
FIG. 4A is a perspective view of a newly invented structure of 6-aminoethoxy-6-deoxy-alpha-galactosylceramide, a novel glycolipid analog of alpha-galactosylceramide, which contains amine group for chemical conjugation to the surface of nanoparticles.
Figure 4B:
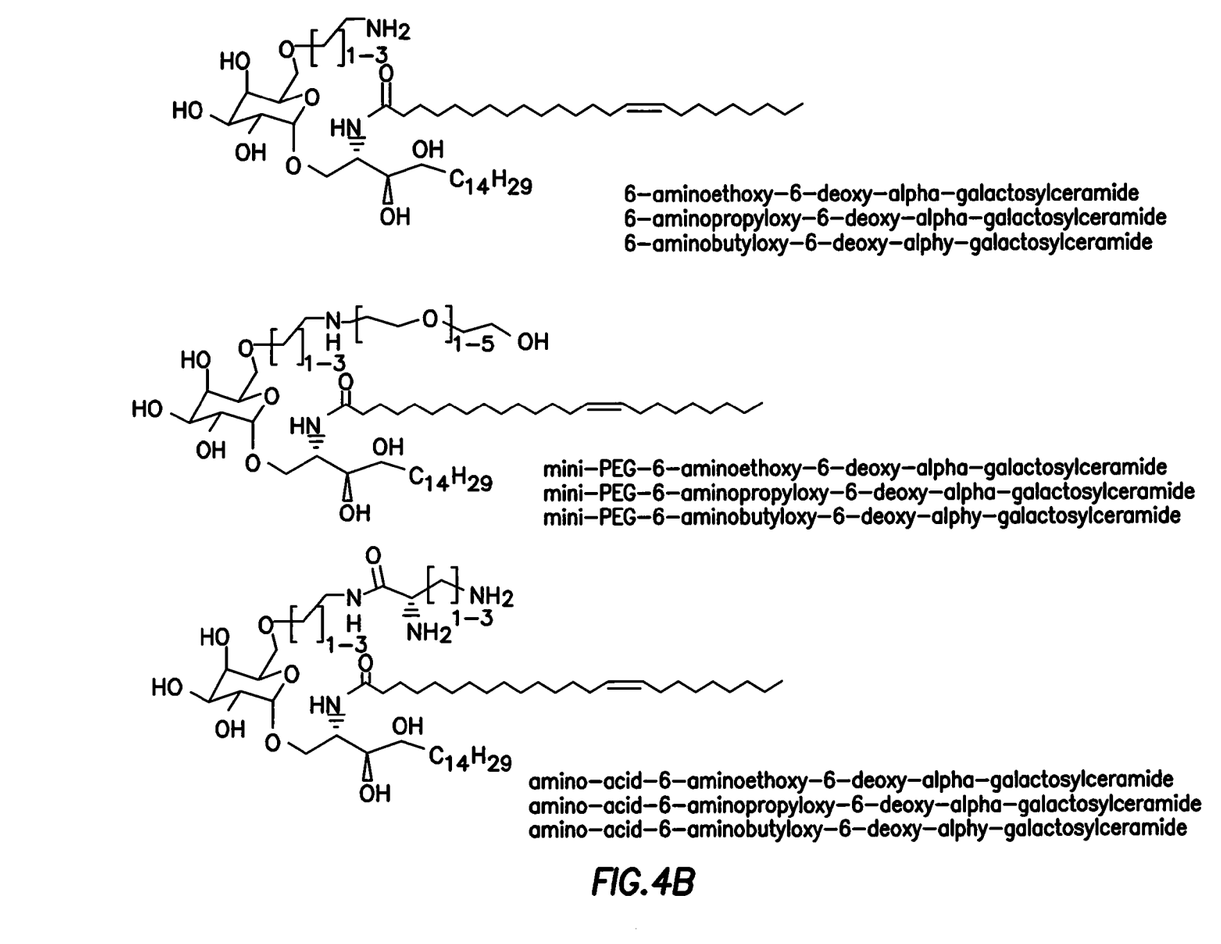
FIG. 4B is perspective views of newly invented structures as follows:
6-aminoethoxy-6-deoxy-alpha-galactosylceramide,
6-aminopropyl-6-deoxy-alpha-galactosylceramide
6-aminobutyloxy-6-deoxy-alpha-galactosylceramide,
amino-acid-6-aminoethoxy-6-deoxy-alpha-galactosylceramide,
amino-acid-6-aminopropyl-6-deoxy-alpha-galactosylceramide,
amino-acid-6-aminobutyloxy-6-deoxy-alpha-galactosylceramide,
mini-PEG-6-aminoethoxy-6-deoxy-alpha-galactosylceramide,
mini-PEG-6-aminopropyl-6-deoxy-alpha-galactosylceramide, and
mini-PEG-6-aminobutyloxy-6-deoxy-alpha-galactosylceramide,
all of which are novel glycolipid analogs of alpha-galactosylceramide containing amine group for chemical conjugation to the surface of nanoparticles.

With reference to FIG. 3, the acyl groups exposed on the surface of nanoparticles can be utilized to conjugate with amine groups through amide linkage (or by non-covalent methods which is not shown in FIG. 3). However, alpha-galactosylceramide does not contain amine groups. Since the 6-OH group of galactose is known to be dispensable for the antigenic activity of alpha-galactosylceramide, some embodiments in accordance with the present invention provide a series of glycolipid analogs as shown in FIG. 4A and FIG. 4B, such as 6-aminoethoxy-6-deoxy-alpha-galactosylceramide, 6-aminopropyl-6-deoxy-alpha-galactosylceramide, 6-aminobutyloxy-6-deoxy-alpha-galactosylceramide, amino-acid-6-aminoethoxy-6-deoxy-alpha-galactosylceramide, amino-acid-6-aminopropyl-6-deoxy-alpha-galactosylceramide, and amino-acid-6-aminobutyloxy-6-deoxy-alpha-galactosylceramide, which contain amine group in 6-OH group of galactose. All of the series of glycolipid analogs allows the formation of amide linkage.

On the other hand, compounds like mini-PEG-6-aminoethoxy-6-deoxy-alpha-galactosylceramide, mini-PEG-6-aminopropyl-6-deoxy-alpha-galactosylceramide, and mini-PEG-6-aminobutyloxy-6-deoxy-alpha-galactosylceramide, can also be conjugated to nanoparticles bearing amine groups.

To avoid antibody response to any additional protein (such as streptavidin-biotin system), alpha-galactosylceramide can also be directly conjugated to nanopolymer materials.

Both alpha-galactosylceramide and polymers are not antigenic in mouse and human. Either covalent or non-covalent conjugates of polymers and alpha-galactosylceramide do not create immuno-reactive epitopes, Exemplary Production Method of Nanoparticle Formulated Glycolipid Antigens A corresponding production method of a nanoparticle formulated glycolipid antigens (6-aminoethoxy-6-deoxy-alpha-galactosylceramide conjugated to PLGA nanoparticles) is provided as follows.

1. Preparation of PLGA Nanoparticles.

The nanospheres can be prepared using nanoprecipitation method in the presence of the stabilizing copolymer. The PLGA, such as PLGA from Absorbable Polymers International (Pelham, Ala., USA), can be dissolved in acetone (0.5% w/v). The polymer solution can be added drop-wise to an aqueous solution containing poloxamine 904, such as poloxamine 904 made by BASF Wyandotte Corporation located in Parsippany, N.J., USA. The mixture can be stirring at room temperature until the organic solvent is completely dried. The resulting nanoparticle dispersions can be passed through a 1 μm filter, and purified by centrifugation. Nanoparticles can be re-dispersed in water, flash-frozen liquid nitrogen and subject to lyophilization. The dry powder formulation can be stored in −20° C. This protocol can provide nanoparticles with the diameter of about 50 nm to 500 nm, depending on the molecular weight of PLGA, stirring rate, and the concentration of surfactant.

2. Preparation of 6-aminoethoxy-6-deoxy-alpha-galactosylceramide, Which Contains Amine Group for Direct Conjugating to PLGA Nanoparticles.

Figure 5A:
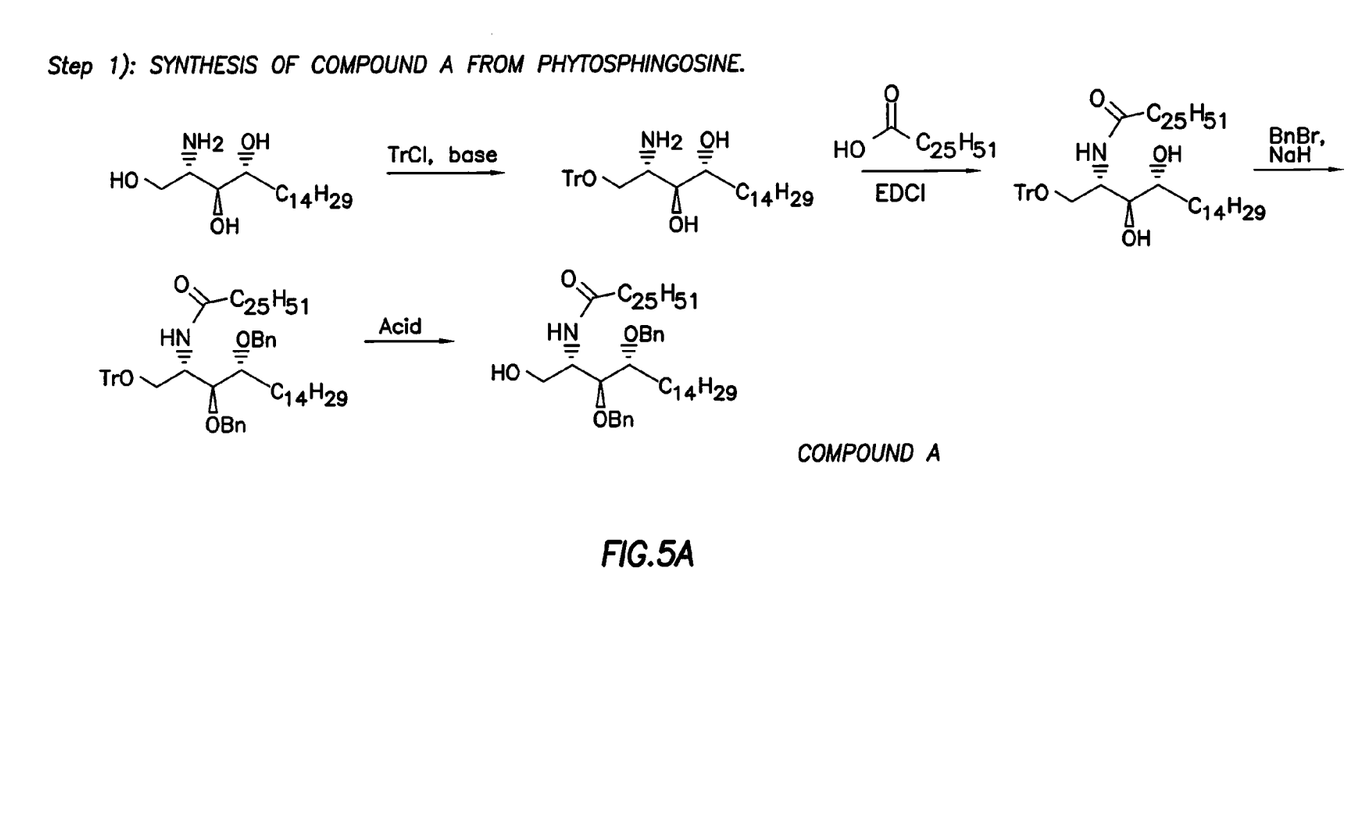
FIG. 5 is a perspective view of a chemical synthesis route for producing 6-aminoethoxy-6-deoxy-alpha-galactosylceramide.
Figure 5B:
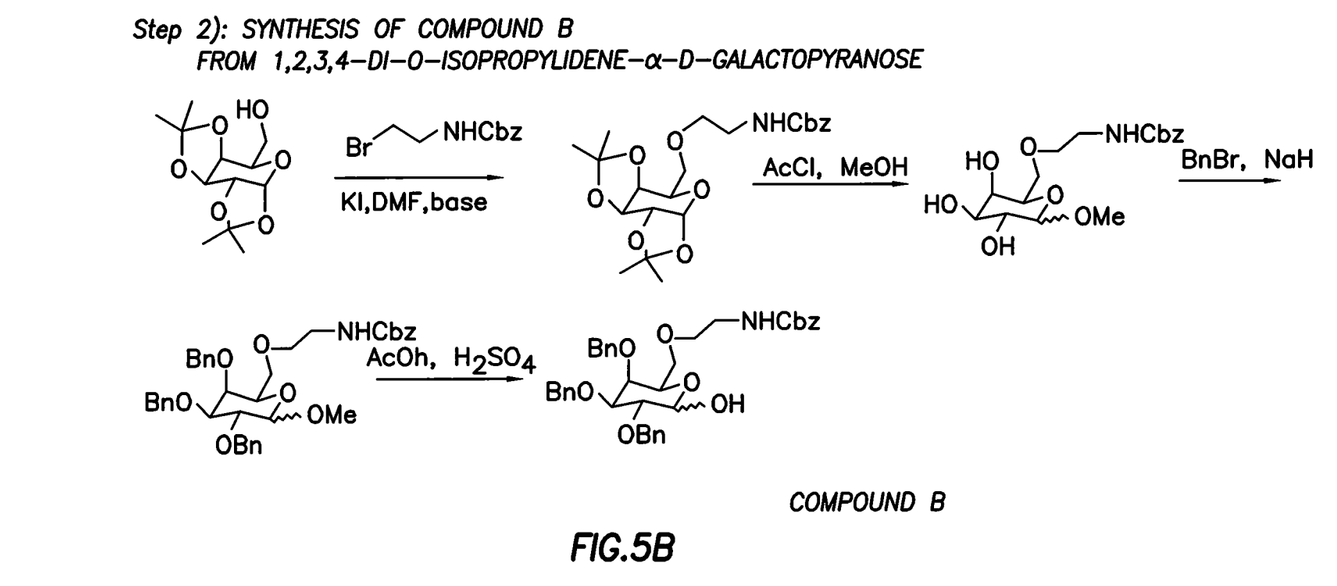
Figure 5C:
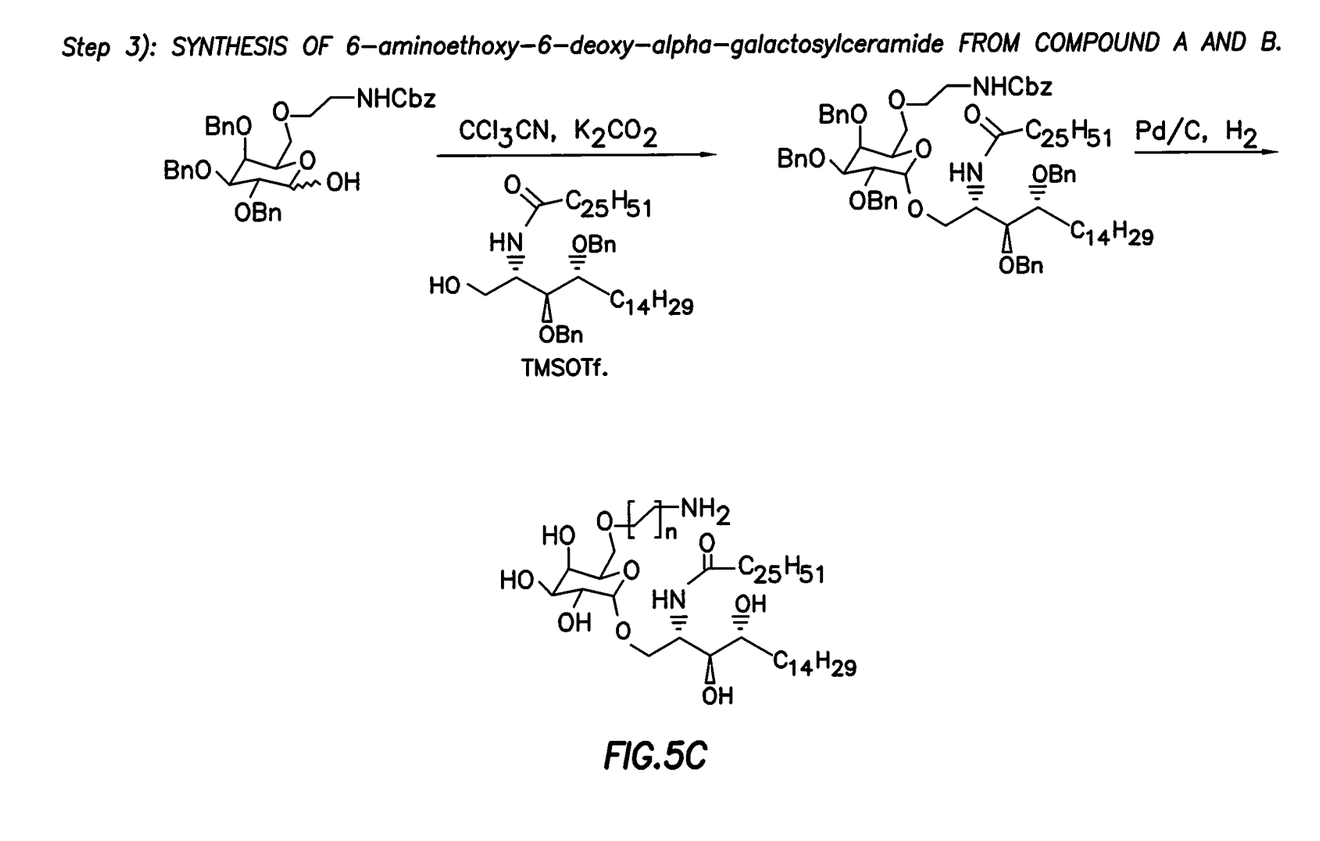

With reference to FIG. 5, step 1 is to synthesize Compound A from Phytosphingosine. Step 2 is to synthesize Compound B from 1,2,3,4-DI-O-ISOPROPYLIDENE-α-D-GALACTOPYRANOSE. Step 3 is to synthesize 6-aminoethoxy-6-deoxy-alpha-galactosylceramide from Compound A and B.

3. Conjugation of 6-aminoethoxy-6-deoxy-alpha-galactosylceramide to PLGA nanoparticles, 6-aminoethoxy-6-deoxy-alpha-galactosylceramide can be conjugated to PLGA particles at 1% and 10% (w/w ratio).

Results of Immunstimulatory Activity and Antitumor Activity of the Drug of Nanoparticle Formulated Glycolipid Antigens

EXPERIMENTAL EXAMPLE 1

Immunstimulatory Activity of the Drug of the Present Invention

1. In Vivo Stimulation of NKT Cells by Nanoparticle Formulated αGalCer:

Nanoparticle containing 1 μg alpha-galactosylceramide was injected to C57BL6 mice, with non-conjugated nanoparticles as negative control. In parallel, we studied soluble form of alpha-galactosylceramide.

2. The Repeated In Vivo NKT Cell Stimulation:

C57/BL6 mice were purchased from the Jackson Laboratory (Bar Arbor, Me.) and housed in M.D. Anderson Cancer Center animal facilities under standard pathogen free conditions abiding institutional guidelines. 6 weeks old C57BL/6 mice were used for all experiments. 3 mice per group were used for each experiment. 1 μg alpha-galactosylceramide, or nanoparticle formulated alpha-galactosylceramide in 200 μL PBS was intravenously injected (through tail vein) to each mouse. Mice were treated every 10 days for 3 times. 200 μL of PBS/1% DMSO was used as control.

3. Measurement of IFN-γ Secretion after Each Stimulation:

Mice were bled at 24 hours after each drug treatment. Serum IFN-γ was measured by ELISA using a kit from BD Biosciences (San Jose, Calif.).

4. Results: Nanoparticle Formulated Alpha-Galactosylceramide Overcomes the Anergy of NKT Cells:

Similarly to alpha-galactosylceramide, the first injection of nanoparticle formulated alpha-galactosylceramide elicited cytokine release, peaked at 24-48 hours post injection, as measured by serum IFN-γ concentration. As shown in Table 1, nanoparticle formulated alpha-galactosylceramide induced IFN-γ secretion after each stimulation. In contrast, soluble alpha-galactosylceramide caused IFN-γ secretion only at the first treatment and failed to induce upon subsequent stimulations. Thus our new formulation of alpha-galactosylceramide can repeatedly stimulate NM cells and induce IFN-γ production without leading to anergy

TABLE 1

☐ αGalCer-nanoparticles repeatedly activate NKT cells to produce IFN-γ (pg/mL).

|  | αGalCer-nanoparticles | Nanoparticles w/o αGalCer | αGalCer |
|---|---|---|---|
| x1 injection | 286 ± 39$^a$ | 48 ± 1 | 2601 ± 257 |
| x2 injection | 252 ± 62 | 42 ± 5 | 65 ± 2 |
| x3 injection | 261 ± 102 | 45 ± 3 | 40 ± 11 |

$^a$Data were average of three mice per group along with standard deviation.

EXAMPLE 2

Antitumor Activity of the Drug of the Present Invention

The B16F10 melanoma lung metastasis tumor model was employed to evaluate the anticancer function of the nanoparticle formulated alpha-galactosylceramide drug in mice. 48 hours after drug treatment, 1×10$^5$ B16F10 melanoma cells were injected intravenously through tail vein. 14 days after tumor injection, the mice were sacrificed and the tumor nodes formed through metastasis (primary end point) were counted in mouse lung.

Figure 6:
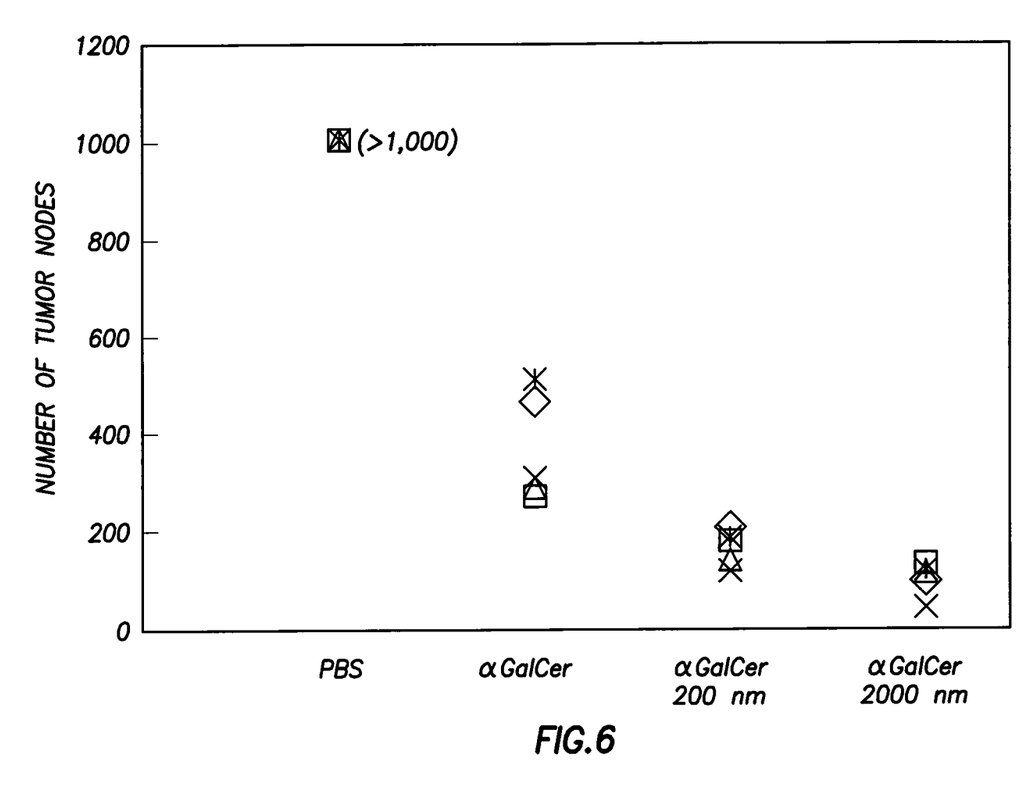
FIG. 6 is a perspective view of an example of the anticancer effect of the present invention.

With reference to FIG. 6, PBS indicates the control mice treated by PBS. αGalCer indicated the mice injected 2 μg soluble form of αGalCer. αGalCer 200 nm indicated the mice injected 2 μg αGalCer bound to 200 nm size of polylactic acid nanoparticles. αGalCer 2000 nm indicated the mice injected 2 μg, αGalCer bound to 2000 nm size of polylactic acid nanoparticles. Each group contained 5 mice (shown as x▲■♦* in FIG. 6). As a result, the nanoparticle formulated alpha-galactosylceramide has significant anticancer effect by showing significantly less number of tumor nodes in mice.

The present invention has been described in terms of specific embodiments incorporating details to facilitate the understanding of principles of construction and operation of the invention. Such reference herein to specific embodiments and details thereof is not intended to limit the scope of the claims appended hereto. It will be readily apparent to one skilled in the art that other various modifications may be made in the embodiment chosen for illustration without departing from the spirit and scope of the invention as defined by the claims.

We claim:

1. A composition comprising:
    a glycolipid simulator of NKT cells; and
    a nanoparticle covalently or non-covalently conjugated with the glycolipid;
wherein the glycolipid is selected from the group consisting of 6-aminoethoxy-6-deoxy-alpha-galactosylceramide, 6-aminopropyl-6-deoxy-alpha-galactosylceramide, 6-aminobutyloxy-6-deoxy-alpha-galactosylceramide, amino-acid-6-aminoethoxy-6-deoxy-alpha-galactosylceramide, amino-acid-6-aminopropyl-6-deoxy-alpha-galactosylceramide, amino-acid-6-aminobutyloxy-6-deoxy-alpha-galactosylceramide, mini-PEG-6-aminoethoxy-6-deoxy-alpha-galactosylceramide, mini-PEG-6-aminopropyl-6-deoxy-alpha-galactosylceramide, and mini-PEG-6-aminobutyloxy-6-deoxy-alpha-galactosylceramide.

2. A composition according to claim 1 wherein the nanoparticle comprises an acyl group exposed on the surface of the nanoparticle and wherein the nanoparticle is conjugated to the glycolipid by means of an amine group positioned on the glycolipid through an amide linkage.

3. A composition comprising:
    a glycolipid stimulator of NK cells;
    a nanoparticle covalently or non-covalently conjugated with the glycolipid, the nanoparticle being composed of a biodegradable polymer, the nanoparticle having a half-life of 48 hours or less in vivo and further wherein the composition has the property of stimulating NKT cells to produce anti-cancer and anti-viral cytokines without causing anergy of NKT cells, wherein the glycolipid is a glycolipid analog of alpha-galactosylceramide with amine groups, further wherein the glycolipid analog of alpha-galactosylceramide is selected from the group consisting of 6-aminoethoxy-6-deoxy-alpha-galactosylceramide, 6-aminopropyl-6-deoxy-alpha-galactosylceramide, 6-aminobutyloxy-6-deoxy-alpha-galactosylceramide, amino-acid-6-aminoethoxy-6-deoxy-alpha-galactosylceramide, amino-acid-6-aminopropyl-6-deoxy-alpha-galactosylceramide, amino-acid-6-aminobutyloxy-6-deoxy-alpha-galactosylceramide, mini-PEG-6-aminoethoxy-6-deoxy-alpha-galactosylceramide, mini-PEG-6-aminopropyl-6-deoxy-alpha-galactosylceramide, and mini-PEG-6-aminobutyloxy-6-deoxy-alpha-galactosylceramide.

4. A composition according to claim 1 wherein the polymer is selected from the group consisting of PLGA, human albumin, polylactic acid, glycolic acid, polycaprolactone, and any copolymers composed by 2 or more than 2 polymers mentioned above.

5. The composition of claim 1, wherein the glycolipid analog is 6-aminoethoxy-6-deoxy-alpha-galactosylceramide.

6. The composition of claim 1, wherein the glycolipid analog is 6-aminopropyl-6-deoxy-alpha-galactosylceramide.

7. The composition of claim 1, wherein the glycolipid analog is 6-aminobutyloxy-6-deoxy-alpha-galactosylceramide.

8. The composition of claim 1, wherein the glycolipid analog is amino-acid-6-aminoethoxy-6-deoxy-alpha-galactosylceramide.

9. The composition of claim 1, wherein the glycolipid analog is amino-acid-6-aminopropyl-6-deoxy-alpha-galactosylceramide.

10. The composition of claim 1, wherein the glycolipid analog is amino-acid-6-aminobutyloxy-6-deoxy-alpha-galactosylceramide.

11. The composition of claim 1, wherein the glycolipid analog is mini-PEG-6-aminoethoxy-6-deoxy-alpha-galactosylceramide.

12. The composition of claim 1, wherein the glycolipid analog is mini-PEG-6-aminopropyl-6-deoxy-alpha-galactosylceramide.

13. The composition of claim 1, wherein the glycolipid analog is mini-PEG-6-aminobutyloxy-6-deoxy-alpha-galactosylceramide.

\* \* \* \* \*